(12) United States Patent
Alhadrami et al.

(10) Patent No.: US 10,962,529 B1
(45) Date of Patent: Mar. 30, 2021

(54) FLUORESCENT PROBE BASED BIOSENSOR AND ASSAY FOR THE DETECTION OF SARS-COV-2

(71) Applicant: King Abdulaziz University, Jeddah (SA)

(72) Inventors: Hani A. Alhadrami, Jeddah (SA); Mohammed Zourob, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/108,263

(22) Filed: Dec. 1, 2020

(51) Int. Cl.
*G01N 33/533* (2006.01)
*C12Q 1/04* (2006.01)
*C12Q 1/37* (2006.01)
*G01N 21/64* (2006.01)

(52) U.S. Cl.
CPC .............. *G01N 33/533* (2013.01); *C12Q 1/04* (2013.01); *C12Q 1/37* (2013.01); *G01N 21/6428* (2013.01); *G01N 2021/6432* (2013.01); *G01N 2021/6439* (2013.01); *G01N 2333/165* (2013.01); *G01N 2333/9513* (2013.01)

(58) Field of Classification Search
CPC ............. G01N 33/533; G01N 21/6428; G01N 2333/9513; G01N 2333/165; G01N 2021/6439; G01N 2021/6432; C12Q 1/04; C12Q 1/37
See application file for complete search history.

(56) References Cited

PUBLICATIONS

Brown et al., "High-Throughput Screening for Inhibitors of the SARS-CoV-2 Protease Using a FRET-Biosensor", Molecules (2020) 25, 4666.
Jullian et al., "N-terminus FITC labeling of peptides on solid support: the truth behind the spacer", Tetrahedron Letters 50 (2009) 260-263.
Kaman et al., "Evaluation of a D-amino-acid-containing fluorescence resonance energy transfer peptide library for profiling prokaryotic proteases", Analytical Biochemistry 44' (2013) 38-43.
Zhu et al., "Identification of SARS-CoV-2 3CL Protease Inhibitors by a Quantitative High-Throughput Screening", ACS Pharmacol. Transl. Sci. (2020), 3, 1008-1016.

*Primary Examiner* — Jennifer Wecker
*Assistant Examiner* — Michael Paul Shimek
(74) *Attorney, Agent, or Firm* — W & C IP

(57) ABSTRACT

A method for detecting a SARS-Cov-2 protease in a biological sample is provided. The method includes contacting the biological sample with a fluorescent probe based sensor, wherein the sensor comprises an L-Histidine-D-aspartic acid peptide substrate, a fluorophore, and a quencher molecule; and detecting the SARS-Cov-2 protease when an increase in fluorescence is observed.

10 Claims, 6 Drawing Sheets

FLUORESCENT PROBE BASED BIOSENSOR AND ASSAY FOR THE DETECTION OF SARS-COV-2

FIELD OF THE INVENTION

The invention is generally related to a fluorescent probe based biosensor useful for the detection of SARS-CoV-2 viral proteases in biological samples.

BACKGROUND OF THE INVENTION

Infectious diseases, including those of viral origin, are the main cause of human pathogenesis and death throughout the world, exceeding even cancer and cardiovascular illnesses (Kannan et al., 2020). Viruses are responsible for 15 million of 57 million human deaths annually worldwide [WHO accessed on 24 Oct. 2020]. Although remarkable technological progress has been made across the globe to identify, monitor, and control many of these emerging and re-emerging infectious diseases, these diseases are becoming an increasing public health concern (Lu et al., 2014).

Coronaviruses are a large viral family that causes illness in animals and humans. In humans, several coronaviruses are known to cause respiratory infections ranging from a mild cold to severe diseases such as Middle East Respiratory Syndrome (MERS) and Severe Acute Respiratory Syndrome (SARS). The most recently discovered coronavirus causes coronavirus disease 2019 (COVID-19) which was announced a pandemic in February 2020. The outbreak of COVID-19 caused by the severe acute respiratory syndrome coronavirus 2 (SARS-CoV-2/2019-nCoV) poses a serious threat to global public health and local economies [WHO accessed on 24 Oct. 2020]. COVID-19 is a highly pathogenic viruses and has caused hundreds of thousands of serious illnesses and human life losses all over the world.

Severe respiratory illness in humans due to COVID-19 was first reported in December 2019 at Wuhan city in China. People at high risk to die due to infection with COVID-19 are those who have chronic diseases such as diabetes, renal failure, chronic lung disease, and immunocompromised patients. The incubation period of COVID-19 varies between 2 and 14 days (WHO accessed on 25 Oct. 2020). COVID-19 might cause mild illnesses, severe pneumonia, severe respiratory syndrome, and multi-organ failure. Other symptoms of COVID-19 infections are fever, anorexia, nausea, vomiting, abdominal pain, diarrhea, and disseminated intercellular coagulation.

COVID-19 cases must be confirmed by the WHO, CDC and MOHSA recommended laboratory tests. The cases must be screened by RT-PCR via targeting three genes: RdRP gene, E gene and N gene (Corman et al., 2020). However, there are many other clinical methods available for the diagnosis of COVID-19 such as ELISA, Western blots that detect specific COVID-19 proteins or Northern blot hybridization targeting specific COVID-19 genes (Kannan et al., 2020).

Recently, protease-based nanobiotechnology has played a potential role in the detection and identification of pathogenic microorganisms. Peptide hydrolase, commonly known as proteases, cleave the peptide bonds in the macromolecular protein and short peptides. As this reaction is irreversible, the proteases must be properly regulated for their activity and specificity in biological processes. Proteases play an important role in life from viruses to vertebrates. The activation energy of the amide bond hydrolysis is low, however, it is very slow at normal temperature and pH. It might take hundreds of years to break a peptide bond without protease catalysis. Relatively, proteases cleave approximately one million bonds per second (Castro et al., 2011). Proteases regulate the metabolic and physiological functions in most living organisms. Many bacteria and viruses play a major role in virulence by secreted proteases (Maeda, 1996). These proteases can degrade the host membrane proteins to enter the host cell and cause pathogenicity by replication of viruses or bacteria within the host cells.

Nucleic acid amplification techniques such as PCR (Corman et al., 2020; Corman et al., 2012), nucleic acid sequence-based amplification (NASBA) (Udugama et al., 2020), next-generation sequencing (NGS) (Kustin et al., 2019) and Lawrence Livermore microbial detection array (LMDA) (Keightley et al., 2005) are pioneers in the identification of human viral genome from the clinical samples. Although these methods are sensitive, the mutation rate is high, which leads to false results. NASBA is a highly sensitive method, however, this method is not used widely due to the high cost.

Novel viral diagnostic methods that are low cost and highly sensitive and specific are needed.

SUMMARY

Described herein are simple, low cost, and reliable fluorescence resonance energy transfer (FRET) biosensors for the detection of the SARS-CoV-2 virus using the activity of viral secreted proteases. Peptides labeled with a fluorophore and a quencher at both ends are cleaved in the presence of protease, therefore separating the fluorophore and the quencher leading to a high fluorescent signal.

An aspect of the disclosure provides a method for detecting a SARS-Cov-2 protease in a biological sample, comprising contacting the biological sample with a fluorescent probe based sensor, wherein the sensor comprises an L-Histidine-D-aspartic acid peptide substrate, a fluorophore, and a quencher molecule; and detecting the SARS-Cov-2 protease when an increase in fluorescence is observed. In some embodiments, the biological sample is respiratory mucosa.

In some embodiments, the fluorophore is a xanthene dye, such as fluorescein isothiocyanate (FITC). In some embodiments, the fluorophore is at the N-terminus of the FRET sensor. In some embodiments, the fluorophore is coupled to an amino acid linker.

In some embodiments, the quencher molecule is a non-fluorescent quencher molecule, such as 4-(4'-dimethylaminophenylazo)-benzoic acid (Dabcyl). In some embodiments, the quencher molecule is at the C-terminus of the FRET sensor. In some embodiments, the quencher molecule is coupled to lysine.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Figure 1A:
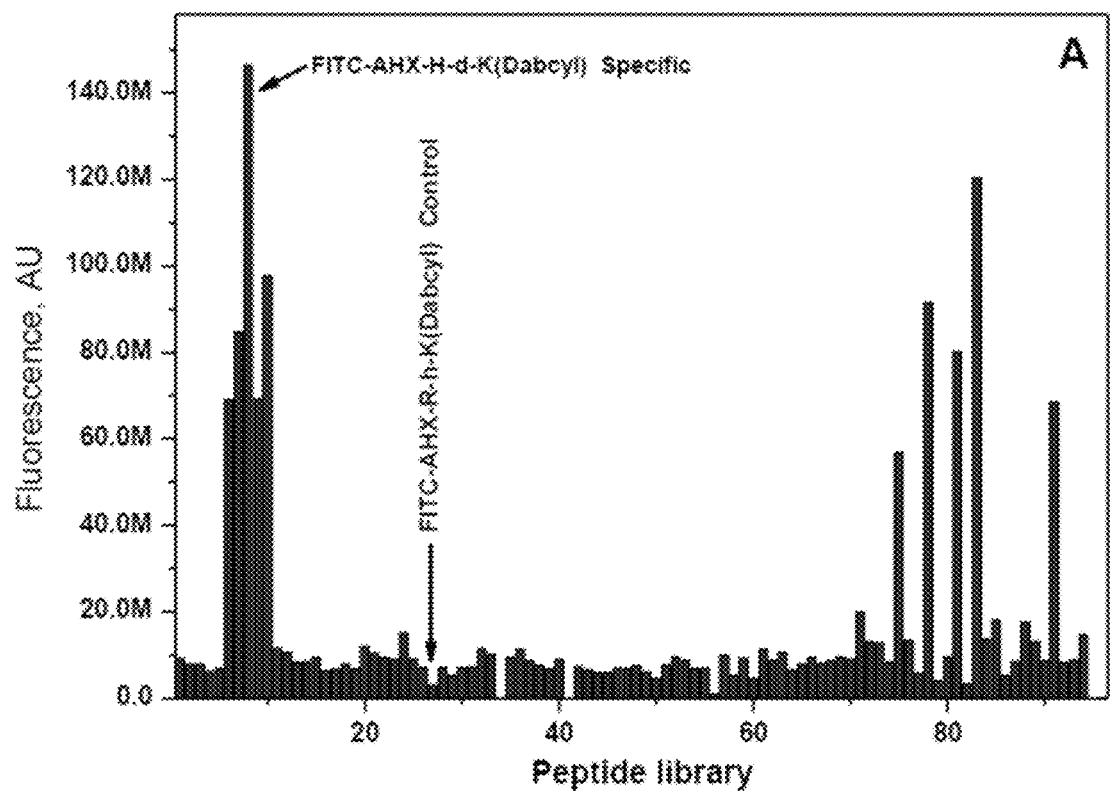
FIGS. 1A-B. (A) The change in the fluorescence signal of 115 different fluorogenic substrates presence of $10^8$ pfu/ml at 37° C. (B) The FRET substrates with significant increase in the fluorescence signal upon incubation with $10^8$ pfu/ml of Covid-19 viral particles at 37° C. The dotted line represents the threshold fluorescence. The samples were excited at 485 nm and the fluorescence was observed at 535 nm.

FIG. 4. The plot of change in the fluorescence of FITC-Ahx-H-d-(Dabcyl)peptide substrate against the various concentrations of Covid-19 live virus ($10^8$-10 pfu/ml) after 3 hours of incubation at 37° C. The samples were excited at 485 nm and the fluorescence was observed at 535 nm. The standard errors were calculated from the three different measurements.

FIG. 5. Change in the fluorescence of FITC-Ahx-H-d-(Dabcyl) peptide substrate in the presence Covid-19 live virus, Mers-CoV ($10^8$ pfu/ml) and PBS buffer after 3 hours of incubation at 37° C. The samples were excited at 485 nm and the fluorescence was observed at 535 nm. The standard errors were calculated from the three different measurements.

FIG. 6. Scheme of exemplary FRET assay.

DETAILED DESCRIPTION

Embodiments of the disclosure provide methods for detecting a SARS-Cov-2 protease in a biological sample. The SARS-CoV-2 proteases that are detectable include main protease $M^{pro}$ (also referred to as $3CL^{pro}$) and the papain-like protease $PL^{pro}$. The biological sample is contacted with a fluorescent resonance energy transfer (FRET) probe/sensor comprising a peptide substrate, a fluorophore, and a quencher molecule.

As used herein, FRET is a proximity assay based on the non-radiative transfer of energy, i.e., a transfer of energy which occurs without emission of photons, between the fluorescent donor molecule and the acceptor molecule (Chinnappan et al., 2013; Raja et al., 2006) (FIG. 6). In general, the donor and the acceptor are in very close proximity in the fluorogenic peptides and show low fluorescence due to the internal quenching. However, the hydrolysis of the peptide bond between the donor and the acceptor leads to the physical separation of the FRET pairs and a subsequent increase in fluorescence (FIG. 6). An increase in the fluorescence intensity can be monitored at the emission peak of the fluorophore, which is proportional to the activity of the enzyme. The fluorescence kinetics data implies the quantity of the enzyme activity and hydrolysis rate of the specific peptide bond by the protease.

In some embodiments, the FRET sensor comprises a peptide substrate that is specifically and efficiently cleaved by a SARS-Cov-2 protease. In some embodiments, the substrate is a dipeptide substrate, e.g. as shown in Table 1. In some embodiments, the substrate comprises an L-amino acid and a D-amino acid. D-amino acids are amino acids where the stereogenic carbon alpha to the amino group has the D-configuration. For most naturally-occurring amino acids, this carbon has the L-configuration. D-amino acids are most occasionally found in nature as residues in proteins. They are formed from ribosomally-derived D-amino acid residues. In some embodiments, the substrate comprises L-Histidine and D-aspartic acid.

Exemplary suitable fluorophores include, but are not limited to, xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G) (emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc.; BODIPY dyes and quinoline dyes. Other suitable fluorophores include quantum dots and carbon dots.

The fluorophore as described herein may be at the N- or C-terminus of the FRET sensor. In some embodiments, the fluorophore is coupled with a linker or spacer such that the linker or spacer is in between the fluorophore and the peptide substrate which is cleaved by the protease. In some embodiments, the linker contains 10 amino acids or less, e.g. 10, 9, 8, 7, 6, 5, 4, 3, 2, or 1 amino acid(s). In some embodiments, the linker is a 6-aminohexanoic acid, Ahx linker. Other suitable linkers/spacers include C4 to C18 linkers, polymeric linkers, etc.

A quencher can absorb electromagnetic radiation and dissipate it as heat, thus remaining dark. Example quenchers that be used in accordance with some embodiments herein include 4-(4'-dimethylaminophenylazo)-benzoic acid (Dabcyl), dimethylaminoazobenzenesulfonic acid (Dabsyl), other non-fluorescent quenchers, such as black hole quencher 1 (BHQ-1) or BHQ-2 (Biosearch), IOWA BLACK FQ (IDT), and IOWA BLACK RQ (IDT). Suitable quenchers include organic molecules, graphene, and other carbon-based material quenchers. In some embodiments, the quencher is selected to pair with a fluorophore so as to absorb electromagnetic radiation emitted by the fluorophore.

The quencher as described herein may be at the N- or C-terminus of the FRET sensor. In some embodiments, the quencher is coupled with lysine residue such that the lysine is in between the quencher and the peptide substrate which is cleaved by the protease.

The biological sample may be any patient sample in which SARS-CoV-2 proteases are present. Suitable biological samples include respiratory or nasal mucosa, saliva, urine, whole blood, serum, etc.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

The novel coronavirus (SARS-CoV-2) has caused a global pandemic, which creates a need for the urgent development of diagnostic and therapeutic methods. There are several methods available for the detection and diagnosis of SARS-CoV-2 such as RT-PCR, immune assays, DNA sequencing and direct visualization of the virus, however, they are time-consuming and unsuitable for point of care applications. In this study, we have developed a highly specific, sensitive and quantitative assay for the rapid detection of SARS-CoV-2 by fluorescence resonance energy transfer (FRET) assay. The total extracellular protease proteolytic activity from the virus is used as the biomarker. Fluorogenic dipeptide substrates having a fluorophore and a quencher at the N- and the C-terminals respectively is used as the biosensor. When the viral protease hydrolyzes the peptide bond between the two specific amino acids, there is a significant increase in the fluorescence signal. The specific fluorogenic peptide (H-d) produces a high fluorescence signal. A calibration plot was obtained from the change in the fluorescence intensity against the different concentrations of the viral protease. The lowest limit of detection of this method was determined to be 9.7±3 pfu/ml. The cross-reactivity of the SARS-CoV-2 specific peptide was tested against the MERS-CoV which does not affect the fluorescence signal. A significant change in the fluorescence signal with the patient samples indicates that this FRET-based assay can be applied for the rapid diagnosis of SARS-CoV-2 patients.

Materials

Vero E6 cells (ATCC® number 1568) were purchased from the American Type Culture Collection (ATCC). Dulbecco's Eagle medium (DMEM) and fetal bovine serum (FBS), streptomycin and penicillin, HEPES, agarose, paraformaldehyde, crystal violet. PBS, DMSO were purchased from Sigma-Aldrich (Gillingham, UK). Dipeptide library was purchased from Pepmic Co Ltd (Suzhou, China).

Experimental Methods

Cell Line and SARS-CoV-2 Propagation

Vero E6 cells (ATCC® number 1568) were maintained and grown in Dulbecco's Eagle medium (DMEM) containing 10% fetal bovine serum (FBS) as described by (Al-Amri et al., 2017). SARS-CoV-2/human/SAU/85791C/2020 (Gene accession number MT630432.1) was isolated from a human nasopharyngeal swab confirmed positive by RT-PCR. IRP number H-02-K-076-00520-298 was obtained from the Saudi Ministry of Health to use patient samples. All experiments involved in live SARS-CoV-2 were performed following the international recommended safety measures and precautions in Biosafety Level 3 Facility at the Special Infectious Agent Unit, King Fand Medical Research Center, King Abdulaziz University, Saudi Arabia.

SARS-CoV-2 was propagated and titrated using Median Tissue Culture Infectious Dose (TCID50). In brief, SARS-CoV-2 was inoculated on 90%-95% confluent Vero E6 cells in a T175 tissue culture flask and incubated at 37° C. for 1 hour in a humidified 5% $CO_2$ incubator with shaking every 15 min. Then, 25 ml of viral inoculation medium (DMEM supplemented with 10 mmol/L HEPES, 1% streptomycin and penicillin, and 2% FBS) was used to replace the inoculum. The cells were then incubated at 37° C. in a humidified 5% $CO_2$ incubator for 72 hours or until 90% of cells illustrated CPE (cytopathic effect). The supernatant was then harvested and centrifuged at 500×g for 5 min at room temperature. Ultimately, SARS-CoV-2 was aliquoted and stored at −80° C. and plaque assay was used to determine the virus titer and TCID50. MERS-COV was isolated from human nasopharyngeal swab with confirmed positive by RT-PCR. The MERS-COV positive sample was inoculated on the 95% confluent Vero E6 cells and finally, the virus was harvested as described above in the propagation of SARS-COV-2.

Plaque Assay

Plaque assay was conducted as previously described by (Coleman and Frieman, 2015). In brief, DMEM medium was used to grow $1\times10^5$/mL Vero E6 cells. Every well of six-well tissue culture plates were seeded with 2 ml Vero E6 cells and incubated at 37° C. overnight. Serial dilution for each sample (starting from $10^{-1}$) was performed in the inoculated DMEM, and 200 µL of each dilution were transferred to the Vero E6 cell monolayers and incubated at 37° C. for 1 hour with shaking every 15 min. Overlay DMEM with 0.8% agarose was then added to replace the inoculum and incubated at 37° C. for 3-4 days. Subsequently, the overlay was removed, and 4% paraformaldehyde was used for 15 min to fix the cells. Crystal violet was used to stain the cells and plaques were counted to determine SARS-CoV-2 titer as Plaque-Forming Units (PFU/mL). TCID50 for SARS-CoV-2 was calculated as $3.16\times10^5$.

Peptide Library Design

The peptide library consists of 115 substrates with two amino acids of the same type or different types including D-amino acids. The library substrates are FRET-based fluorogenic peptides, each peptide has two amino acids of two L-amino acids, or C-terminal L-amino acid and N-terminal D-amino acid, or two D-amino acids. The upper-case letters represent L-amino acids and the lower-case letter represents D-Amino acids. The FITC (Fluorescein isothiocyanate) and the dabcyl, [4-((4-(Dimethylamino)phenyl)azo)benzoic acid] were introduced at both ends of all the substrates. 6-aminohexanoic acid, Ahx linker was introduced between the FITC fluorophore and the N terminal amino acids and lysine was introduced between the C-terminal amino acids and the dabcyl quencher molecule. The combination of different dipeptide substrates has been validated (Kaman et al. 2011, Kaman et al. 2013).

Identification of SARS-COV-2 Specific Substrate by FRET Assay

SARS-COV-2 specific peptide was identified from the library of 115 FRET substrates by high throughput screening. All the fluorogenic peptides with FITC and the dabcyl were added to the wells of 96 well fluorescence microtiter plate. The proteolytic activity of the COVID-19 protease on the individual substrates was monitored from the change in the fluorescence of the FITC at its emission maxima. 0.5 µL of each peptide from 800 µM solution and 50 µl PBS was mixed with 50 µl of SARS-COV-2 total protease (the supernatant of the overnight culture media). Culture media was used as a negative control. The change in the fluorescence intensity of FITC was monitored every 2 minutes for 2.5 hours at 37° C. The samples were excited at 485 nm and the emission was observed at 535 nm. The relative fluorescence unit (RFU) change in each sample with time was calculated by subtracting the sample fluorescence values from the negative control values. The protease activity on the substrate reflects the change in the RFU per minute (RFU/min). The specific peptide with the highest RFU/m is the most specific to SARS-CoV-2. L-Histidine-D-aspartic acid FITC-Ahx-H-d-K(Dabcyl) was found to be the most active peptide in the presence of SARS-CoV-2 protease. FITC-Ahx-H-d-K(Dabcyl) dipeptide is used for further studies.

Real-Time Fluorescence Kinetics of SARS-CoV-2 Specific FRET Substrate

Figure 1B:
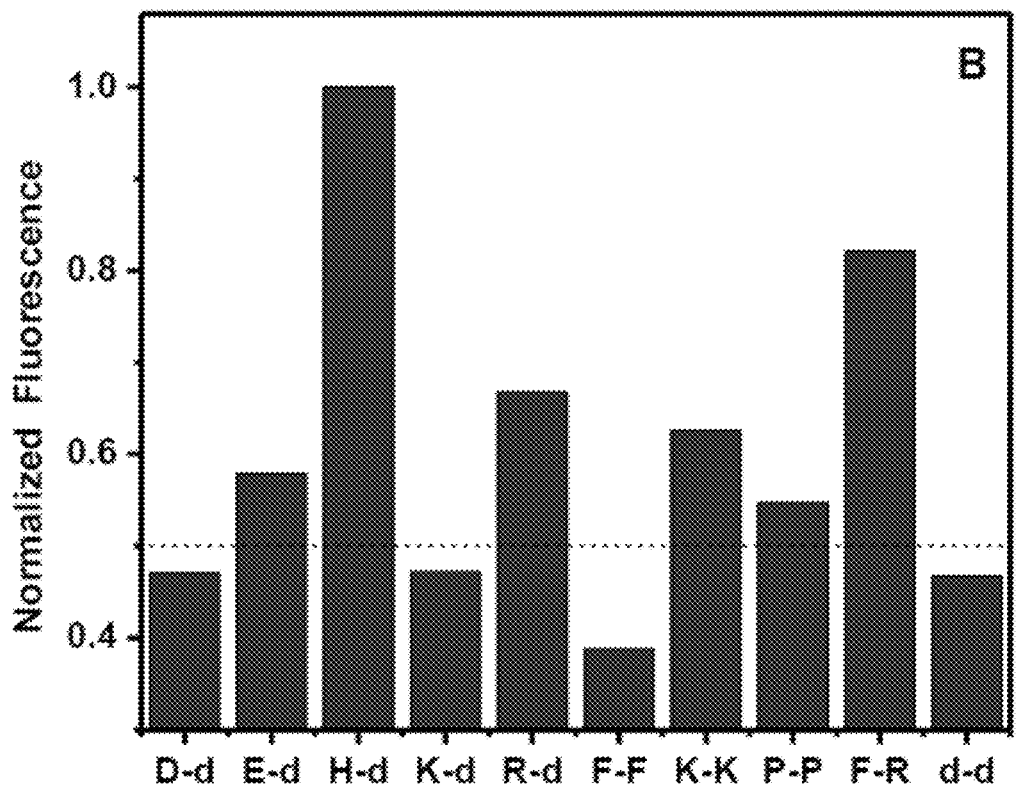

The proteolytic activity of SARS-CoV-2 protease on the fluorescence of the FITC-Ahx-H-d-K(Dabcyl) fluorogenic peptides have been studied. A constant amount (4 µM) of the H-d peptide in PBS buffer was added to nine different wells of the microtiter plate. Live SARS-COV-2 viral solution containing $10^8$ pfu/ml to $10^1$ pfu/ml was added to each well containing the specific peptide. The change in the fluorescence was monitored at 535 nm with the excitation at 495 nm. The fluorescence of FITC in each well was recorded every two minutes for three hours. The well with the only dipeptide without the live virus was considered as a negative control. The fluorescence values were obtained by subtracting negative control values from the sample values. The raw plot of fluorescence signal change against time for individual samples was presented in the FIG. 1A. The percentage change was calculated by $(F-F_0/F_0)\times100$. FIG. 1B represents the exponential fluorescence signal growth of FITC-Ahx-H-d-K(Dabcyl) peptide in the presence of $10^8$ pfu/ml at different intervals of time.

Detection Limit and Specificity

The sensitivity is determined by the ability of the sensor to detect the lowest concentration of the analyte. The sensitivity of the FITC-Ahx-H-d-K(Dabcyl) peptide was determined from the calibration plot, obtained from the fluorescence of the peptide with different concentrations of the SARS-COV-2 live virus in the dynamic range of $10^1$-$10^8$ pfu/ml. The fluorescence intensity of each sample against the corresponding concentrations of the protease was shown in FIG. 2A. The specificity of the peptide against the other closely associated virus such as MERS-CoV has been tested under the same conditions. The fluorescence signal change in the presence of SARS-CoV-2 positive patient sample has been observed and the corresponding pfu/ml was calculated from the standard calibration plot.

Real-Time RT-PCR for SARS-COV-2 Patient Samples

PowerChek™ 2019-nCoV Real-time PCR Kit (Cat No. R6900TD—100 Samples) was used to perform the RT-PCR test for nasopharyngeal swabs collected from SARS-COV-2 infected patients. The kit was purchased from Kogenebiotech Co., Ltd. Republic of Korea, and it was approved by FDA. The kit was utilized according to the manufacturer's instructions, and it targets the RdRp gene for 2019-nCoV in nasopharyngeal swab and sputum. In brief, ExiPrep™ 96 Lite was used with ExiPrep™ 96 Viral DNA/RNA Kit (BioNEER Corp) to extract SARS-COV-2 RNA. PowerChek™ provides a one-step real-time RT-PCR premix with specific primers and probes. PCR mixture was prepared by adding 11 uL of RT-PCR Premix, 4 µL of each primer/probe mix and 5 µL of RNA sample to reach a total reaction volume of 20 uL. The real-time RT-PCR reaction was conducted by programing the LightCycler® 480 Instrument II using the following temperature profile: 50° C. for 30 min (1 cycle), 95° C. for 10 min (1 cycle), 95° C. for 15 sec (40 cycles) and 60° C. for 1 min (40 cycles). The fluorescence curves were analyzed on FAM fluorescence detection channel for the RdRp gene-2019-nCoV and JOE (VIC or HEX) for the internal control. The result was considered positive if the corresponding fluorescence accumulation curve crosses the threshold line. Negative, positive and internal controls were used and their results must be passed for the run to be accepted.

Results and Discussion

Enzymes are capable of hydrolyzing the peptide bond between the naturally occurring amino acids. The composition of the amino acid pair determines the specificity of the substrate for the enzyme of interest. The favorable unique conformation of amino acids and their chemical structure with their side chains between the peptide links are important parameters for the hydrolysis of the peptide bond by enzymes. Under pathological conditions, the proteolytic activity of enzymes plays a major role in many pathological processes. Therefore, the identification of these enzymes is important for understanding the mechanism and retarding the pathological enzymatic process.

High Throughput Screening for SARS-COV-2 Specific Peptide

The SARS-COV-2 protease proteolytic activity was tested against 115 different fluorogenic peptides to identify the specific substrate from the fluorescence signal. We used dipeptides of L-amino acids, D-amino acids and combinations of both. L-amino acids are present in the major natural proteins. Some bacterial species produce D-isomers as well in the milli-molar range in the cell wall (Lam et al., 2009). Therefore, it is assumed that the protease produced from the bacteria may have the combination of both L and D-amino acids (Aliashkevich et al., 2018), and it might digest D-amino acid substrates (Kaman et al., 2013). *Listeria monocytogenes* protease specifically cleaves the D-amino acid peptides faster than the L-amino acids of the same peptide (Alhogail et al., 2016). SARS-COV-2 main protease ($M^{pros}$) specific substrate and 3 L protease ($3L^{pro}$) substrate have been identified using FRET assay by high throughput screening assay (Rut et al., 2020; Zhu et al., 2020). We used dipeptides with a single peptide bond between the amino acids which is the only peptide bond that undergos hydrolysis and induces the fluorescence signal (Kaman et al., 2011). SARS-COV, and SARS-COV-2 M protease-specific substrates have been screened by a high throughput screening method using both natural and unnatural amino acids (Rut et al., 2020; Van de Plassche et al., 2020). In this screening process, the SARS-COV-2 total protease was incubated with the individual FRET substrate for 2 hours at 37° C. Change in the fluorescence intensity of each peptide was compared to find the efficient hydrolysis of the peptide bond by the SARS-COV-2 protease on the specific peptide substrate. The fluorescence signal response due to substrate hydrolysis is illustrated in the FIG. 1A. We chose ten substrates that show considerable fluorescence signal change in the presence of SARS-COV-2 protease (D-d, E-d, H-d, K-d, R-d, F-F, P-P, F-R and d-d). The relative fluorescence intensity of the substrates were tabulated in Table-1. The highest fluorescence change was observed from FITC-Ahx-H-d-K(Dabcyl dipeptide, and we consider this the relative scale of 100%. FITC-Ahx-F-R-K(Dabcyl) shows 82% increase in the fluorescence intensity compared to H-d peptide (FIG. 1B). Interestingly, most of the active peptide has a combination of L- and D-amino acids. More specifically, the L-amino acids at the N-terminal and D-amino acids in the C-terminals with the exception of F-R and d-d. The two highly sensitive peptides, FITC-Ahx-H-d-K(Dabcyl) and FITC-Ahx-F-R-K(Dabcyl) have the L-amino acids with conjugated cyclic side chains and both peptides have carrying the positive charge in one of the amino acids. The results indicate that the SARS-COV-2 specific dipeptide substrate has either the combination of both L- and D-amino acids or only L-amino acids with cyclic side chain and/or positive charge in one of the amino acids. More than 50% of the active peptides having at least one dicarboxylic acid amino acids (aspartic acid or glutamic acid) implies that the presence of dicarboxylic acid amino acids might be one of the favourable factor for the SARS-CoV-2 protease proteolytic activity. SARS-COV-2 protease digest the FITC-Ahx-H-d-K(Dabcyl) efficiently and shows maximum fluorescence intensity after 3 hour of incubation at 37° C. Interestingly, the fluorogenic dipeptide FITC-Ahx-D-d-K (Dabcyl) and FITC-Ahx-d-d-K(Dabcyl) have the same effect on the cleavage of peptide bond independent of L- or D-amino acids (FIG. 1B), indicates that the presence of specific amino acid in the protease binding site and their orientations are important for the peptide bond cleavage in the substrate. The FITC-Ahx-R-h-K(Dabcyl) is very stable in the presence of SARS-COV-2 protease incubated at 37° C. and confirms insignificant increase in the fluorescence intensity after 3 hours. From the fluorescence results, we chose FITC-Ahx-H-d-K(Dabcyl) for further studies and used FITC-Ahx-R-h-K(Dabcyl) as a control.

TABLE 1

Change in the fluorescence signal of different substrates in the presence of SARS-COV-2 protease

| FRET Substrate | Relative fluorescence |
| --- | --- |
| FITC-Ahx-H-d-K(Dabcyl) | 100 |
| FITC-Ahx-F-R-K(Dabcyl) | 82 |
| FITC-Ahx-R-d-K(Dabcyl) | 67 |
| FITC-Ahx-K-K-K(Dabcyl) | 62 |
| FITC-Ahx-E-d-K(Dabcyl) | 58 |
| FITC-Ahx-P-P-K(Dabcyl) | 55 |
| FITC-Ahx-K-d-K(Dabcyl) | 47 |
| FITC-Ahx-D-d-K(Dabcyl) | 47 |
| FITC-Ahx-d-d-K(Dabcyl) | 47 |

Proteolytic Activity of SARS-COV-2 Protease on FITC-Ahx-H-d-K(Dabcyl) Substrate

Figure 2A:
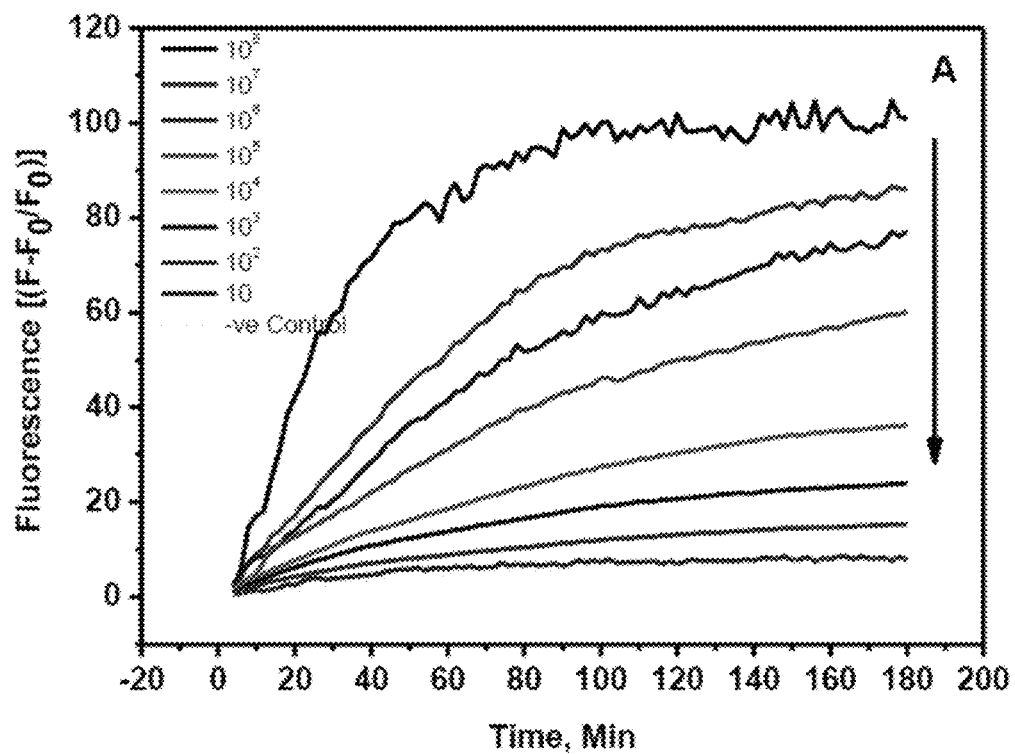
FIGS. 2A-B. (A) The real time fluorescence change in FITC-Ahx-H-d-(Dabcyl)peptide in the presence of various concentrations of Covid-19 live virus in the dynamic range of $10^8$-10 pfu/ml at 37° C. (B) The increase in the fluorescence signal of FITC-Ahx-H-d-(Dabcyl) after incubation with $10^8$ pfu/ml of Covid-19 viral particles at 37° C. The samples were excited at 485 nm and the fluorescence was observed at 535 nm. The standard errors were calculated from the three different measurements.
Figure 2B:
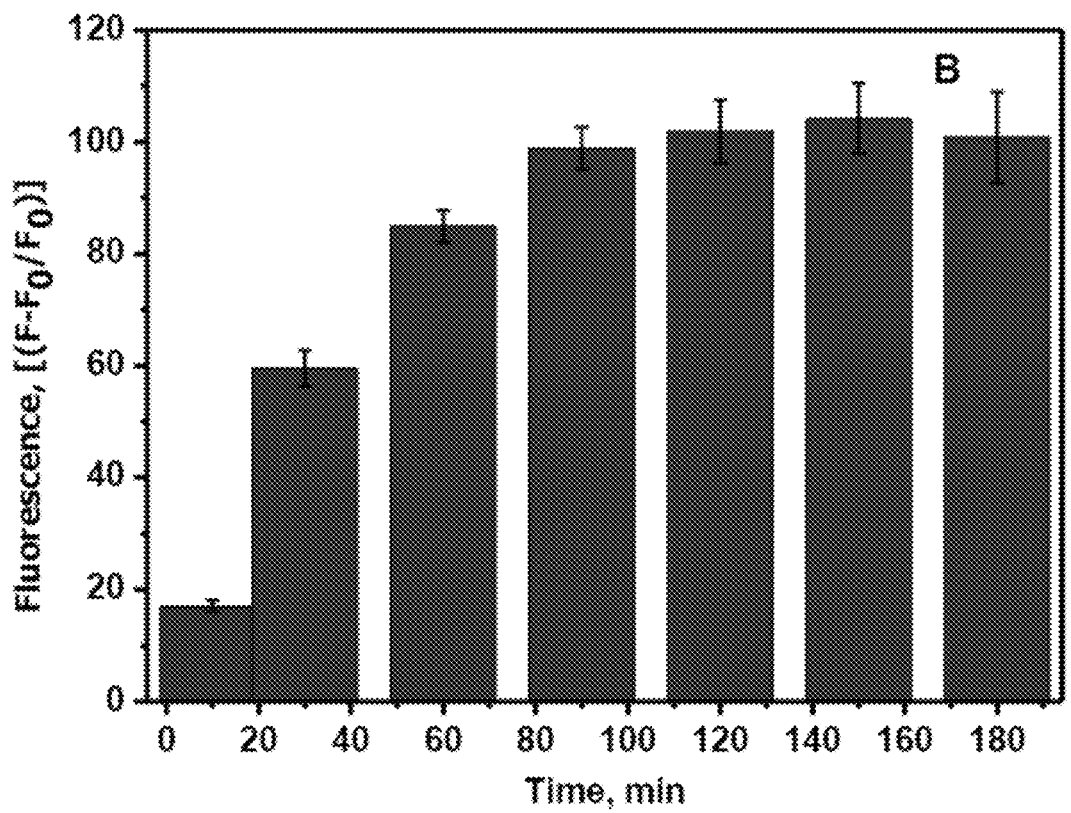

The rate of H-D substrate in the presence of variable concentrations of SARS-COV-2 protease in the dynamic range of $10^1$-$10^8$ pfu/ml. The fluorescence intensity of the FRET substrate increases very rapidly in the presence of $10^8$ pfu/ml of protease (FIG. 2, Black curve). The rate of hydrolysis of the FITC-Ahx-H-d-K(Dabcyl) peptide slowed down with a decrease in the protease concentrations as shown in FIG. 2 curves from top to bottom. There was no significant change in the fluorescence signal of the substrate with $10^1$ pfu/ml of the protease. The fluorescence value was close to the control sample after three hours of incubation at 37° C. (FIG. 2 dotted line). The fluorescence signal of FITC-Ahx-H-d-K(Dabcyl) peptide substrate was increasing linearly with time in the presence of $10^8$ PFU/ml of the protease, indicating that the rate of hydrolysis was very fast in the initial stage of the reaction. The rate decreased over the period of time and the curve plateaus after 1.5 hours. When the protease and the FRET substrates were mixed in the well at the early stage, more number of substrates were available for the protease to digest the H-d peptide link in the FITC-Ahx-H-d-K(Dabcyl) substrate. The protease to substrate ratio decreased with time and fewer substrate numbers became available for the hydrolysis and thus, the increase in the fluorescence intensity was not linear anymore. The kinetics curves of the FITC-Ahx-H-d-K(Dabcyl) with different concentrations were illustrated in FIG. 2A. At the initial stage of the reaction, more number of FITC-Ahx-H-d-K(Dabcyl) substrates are available for the protease to cleave and the reaction was very fast. However, there is less rfu/min after 30 min due to the limited number of substrates available for the protease to interact with. Due to the high protease concentration in this reaction, the change in the protease amount after the reaction was insignificant. Therefore, the rate of the reaction is only dependent on the concentration of the substrate.

SARS-COV-2 Sensing Using FRET Substrate

Figure 3:
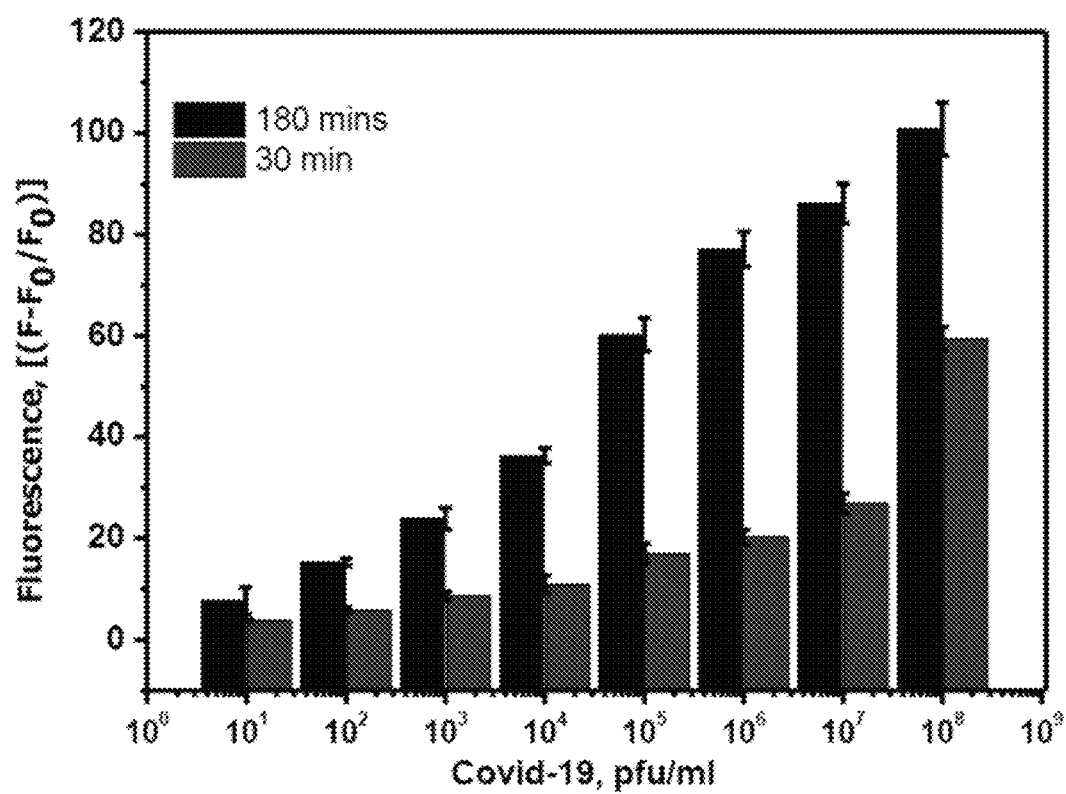
FIG. 3. Change in the fluorescence of FITC-Ahx-H-d-(Dabcyl) peptide substrate in the presence of various concentrations of Covid-19 live virus ($10^8$-10 pfu/ml) after 3 hours of incubation at 37° C. The samples were excited at 485 nm and the fluorescence was observed at 535 nm. The standard errors were calculated from the three different measurements.
Figure 4:
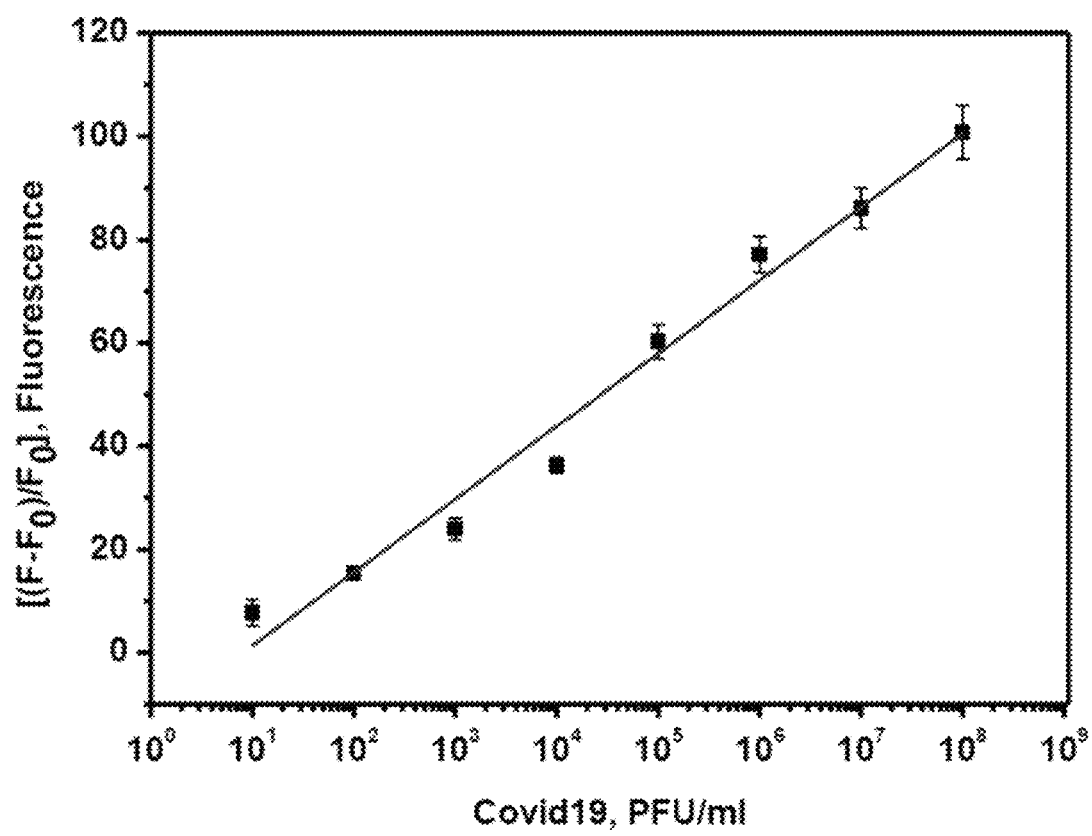

The sensitive detection of SARS-COV-2 was performed by the hydrolysis of the specific peptide bond, between H- and d-amino acids in FITC-Ahx-H-d-K(Dabcyl) substrate by the total protease. When the substrate was incubated with live SARS-COV-2 viral particles, the protease produced as a metabolic by-product, specifically digest the H-d bond rapidly and the FITC donor and the dabcyl acceptor are separated from each other. Therefore, when FITC was excited at 485 nm, the emitted photons were not absorbed by the dabcyl acceptor, because the donor and the acceptor are not in close vicinity and there is no fluorescence quenching. All the emitted photons are monitored as fluorescence emission. The quantitative detection of SARS-COV-2 was achieved by incubating a constant amount of FRET fluorogenic peptide with different concentrations of SARS-COV-2 viral protease ranging from 10 to $10^8$ pfu/ml at 37° C. for 3 hours. Then the fluorescence of FITC in all the samples was monitored and the relative change in the fluorescence was represented in FIG. 3. The left and right bars represent the change in the fluorescence intensity after 180 minutes and 30 minutes, respectively. A significant amount of the reaction was completed within 30 minutes. For example, in the presence of $10^8$ pfu/ml of SARS-COV-2, more than 50% of the reaction is completed within 30 minutes. FIG. 4 shows the plot of the endpoint of fluorescence values after 3 hours against the respective concentrations of the viral particle. FIG. 4 shows the calibration curve which was obtained by plotting the fluorescence signal change against the logarithm of SARS-COV-2 particle (protease) concentration (pfu/ml). The minimum SARS-COV-2 sensing ability of FITC-Ahx-H-d-K(Dabcyl), (limit of detection or LOD), was calculated according to the following formula: 3SD/m, where (SD) is the standard deviation of the fluorescence signal in the absence of SARS-COV-2 particles and (m) is the slope of the straight line obtained from the linear fitting. The calculated LOD of FITC-Ahx-H-d-K(Dabcyl) substrate was found to be 9±3 pfu/ml. Our FRET-based results were compared with the RT-PCR method, which is the gold standard for SARS-COV-2 diagnosis. Table 2 shows the comparison of eight different patient samples (high CT, medium CT and near the cut off CT). The samples with rfu of 77 to 100 showed high CT values, rfu of 25 to 60 have medium Ct values and rfu of 25 and less have a weak Ct values (within the cut off values). The results confirmed that our FRET-based assay is comparable with the standard methods such as RT-PCR. Corman et al developed the RT-PCR method for the detection of SARS-COV-2, and quantified the limit of detection in the range of 2 to 12 copies per reaction (Corman et al., 2020). Van Kasteren et al. compared the commercially available RT-PCR kits with their in-house developed method for the detection of SARS-COV-2. The detection limit of the evaluated kits was in the range of 3 to 10 copies/ml, however, their in-house PCR method has the LOD of 0.91 copies/ml (van Kasteren et al., 2020). Field-effect transistor (FET)-based biosensors have been developed for the sensitive detection of SARS-COV-2 from the clinical sample. The sensing platform was fabricated by coating graphene sheets of the FET with anti-SARS-CoV-2 spike protein antibody. The sensor was tested for antigen protein, cultures virus and specimen from the SARS-CoV-2 positive patients. The sensor was able to detect as low as 16 pfu/ml (Seo et al., 2020). Two high-affinity aptamers against the receptor-binding domain (RBD) of SARS-CoV-2 spike glycoprotein have been selected with the affinity of 5.8 and 19.9 respectively. The aptamer-based recognized receptor is an ideal tool for the development of sensitive and selective aptasensors for the detection of SARS-CoV-2 (Song et al., 2020). The previously reported RT-PCR method is more sensitive than other methods due to amplification processes. However, the other methods are comparable or less sensitive than the reported values by our FRET assay.

TABLE 2

Comparison of FRET assay with RT-PCR.

| Patient Samples | Fluorescence (Relative percentage) | RT-PCR |
| --- | --- | --- |
| Patient 1 | 100 | High |
| Patient 2 | 86.15 | High |
| Patient 3 | 77.12 | High |
| Patient 4 | 60.25 | Medium |
| Patient 5 | 36.28 | Medium |
| Patient 6 | 23.92 | Medium |
| Patient 7 | 15.28 | Weak(~Cut off) |
| Patient 8 | 7.69 | Weak ( ~Cut off) |

Cross-Reactivity of FRET Substrate

Figure 5:
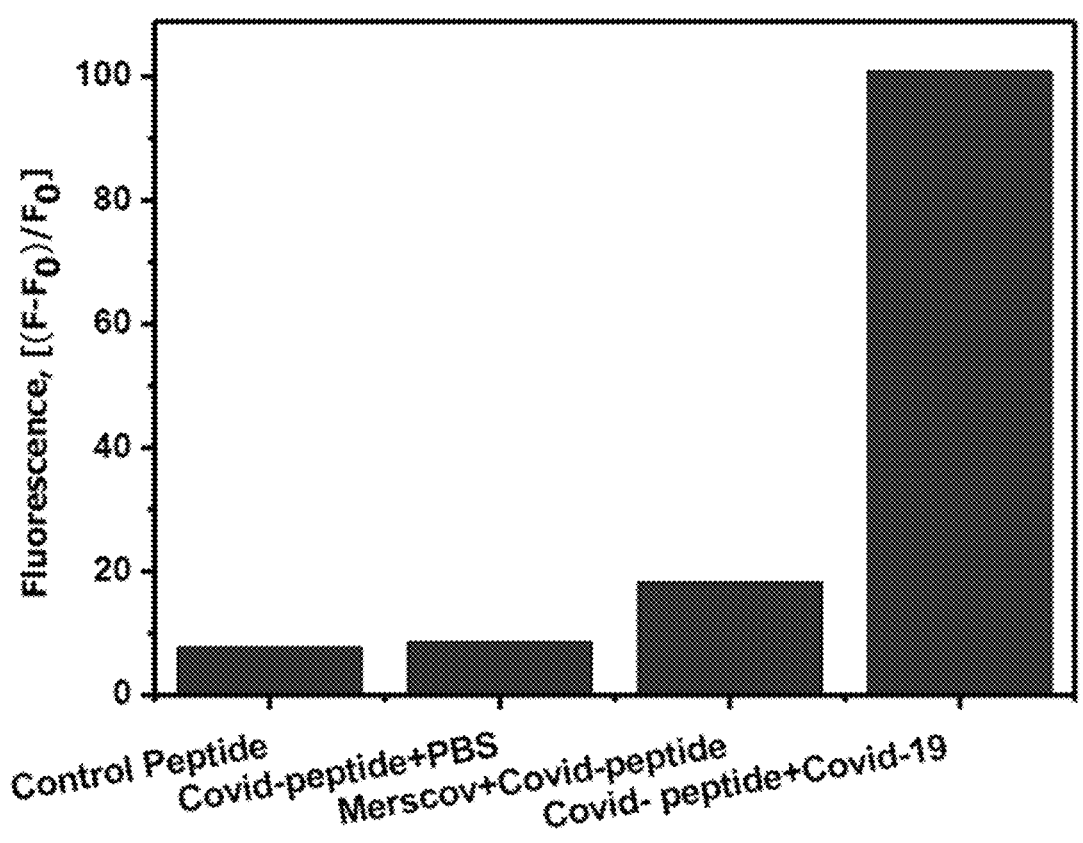
Figure 6:
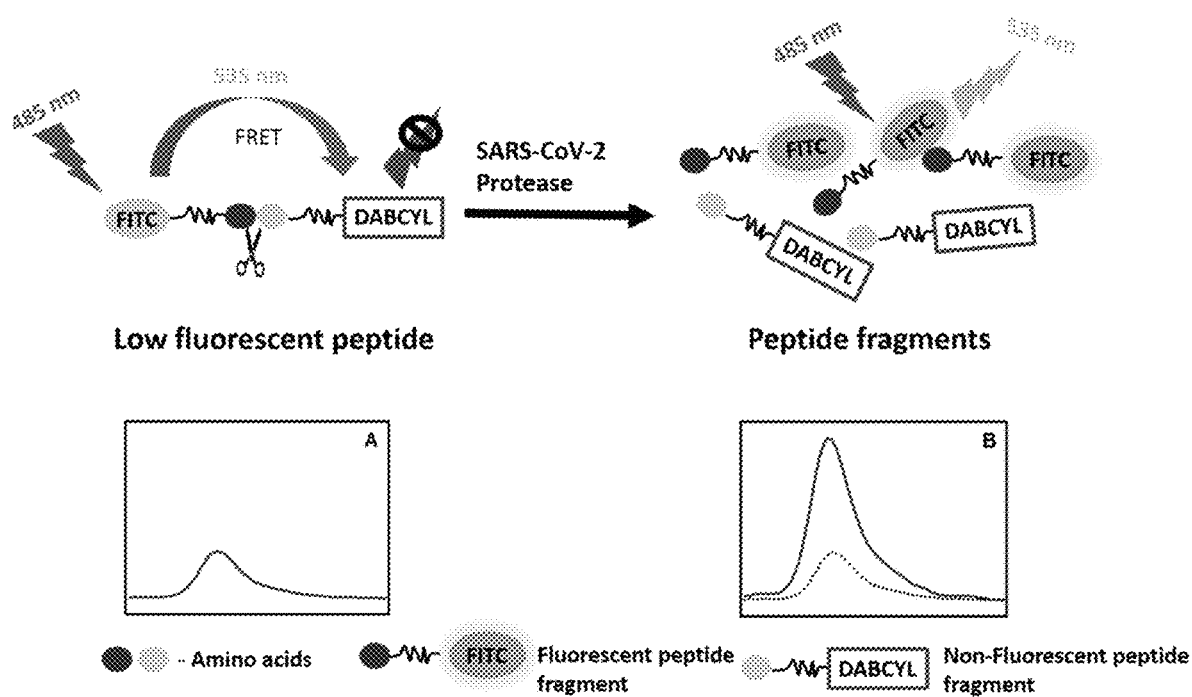

The selective hydrolysis of the H-d peptide bond by the SARS-CoV-2 was validated using the protease obtained from closely associated viruses, such as MERS-COV. The same concentration of MERS-COV viral particles were incubated with FITC-Ahx-H-d-K(Dabcyl) under the similar condition as SARS-COV-2 as mentioned above, and presented in FIG. 5. There was no significant increase in the fluorescence intensity (less than 20%) of FITC-Ahx-H-d-K (Dabcyl) in the presence of MERS-COV virus. The MERS-COV protease does not cleave the H-d peptide link in the FITC-Ahx-H-d-K(Dabcyl) substrate. The change in the fluorescence intensity was close to the FITC-Ahx-H-d-K (Dabcyl) peptide in the absence of SARS-COV-2 virus and control peptide, FITC-Ahx-R-h-K(Dabcyl) which show very minimum fluorescence change in the presence of SARS-COV-2. The results indicate that the fluorogenic substrate, FITC-Ahx-H-d-K(Dabcyl) is very specific to SARS-COV-2. It could specifically digest H-d peptide bond in the mixture of other closely associated viral particles. The specific substrate was validated by incubating the SARS-COV-2 positive patient sample with FITC-Ahx-H-d-K (Dabcyl), and it gave the value of the 34304 pfu/ml from the standard calibration plot. The results suggest that FITC-Ahx-H-d-K(Dabcyl) could be used for the rapid diagnosis of SARS-COV-2 positive samples in bulk in a short time using simple spectrofluorometric measurements.

CONCLUSION

We successfully developed a high-throughput peptide screening for the sensitive detection of SARS-COV-2 from total proteases as a diagnostic marker. Fluorescent Resonance Energy Transfer (FRET) assay has been carried out using fluorogenic dipeptides (L, D or both amino acids in the dipeptide) with a fluorophore and a quencher at both ends. SARS-COV-2 protease specific dipeptide substrates were identified from the quantity of fluorescence signal change. FITC-Ahx-H-d-(Dabcyl) fluorogenic dipeptide is considered as the most specific peptide substrate as it showed the highest fluorescence signal in the presence of SARS-COV-2 total protease. The lowest detection limit of FITC-Ahx-H-d-(Dabcyl) using the protease biomarkers is reported to be 9±3 pfu/ml. The cross-reactivity of the substrate with other closely associated viral proteases such as MERS-CoV has been confirmed from insignificant fluorescence signal change. Clinical patient samples have been used for the validation of the FRET assay, and the values were highly comparable to the standard RT-PCR methods. Therefore, our FRET assay is straightforward, low cost, rapid and easy to handle for the analysis of clinical patient samples.

ACKNOWLEDGMENT

The inventors acknowledge the Financial Support Provided By King Abdulaziz City for Science and Technology (General Directorate for Research & Innovation Support) (GDRIS) (King Abdulaziz University) to Implement This Work Through Fast Track Program For COVID-19 Research Project No. 5-20-01-009-0002.

REFERENCES

Al-Amri, S. S., Abbas, A. T., Siddiq, L. A., Alghamdi, A., Sanki, M. A., Al-Muhanna, M. K., Alhabbab, R. Y., Azhar, E. I., Li, X., Hashem, A. M., 2017 Immunogenicity of candidate MERS-CoV DNA vaccines based on the spike protein. Scientific reports 7, 44875.

Alhogail, S., Suaifan, G. A. R. Y., Zourob, M., 2016. Rapid colorimetric sensing platform for the detection of Listeria monocytogenes foodborne pathogen. Biosensors and Bioelectronics 86, 1061-1066.

Aliashkevich, A., Alvarez, L., Cava, F., 2018. New Insights Into the Mechanisms and Biological Roles of D-Amino Acids in Complex Eco-Systems. Frontiers in Microbiology 9, 683.

Castro, H. C., Abreu, P. A., Geraldo, R. B., Martins, R. C., dos Santos, R., Loureiro, N. I., Cabral, L. M., Rodrigues, C. R., 2011. Looking at the proteases from a simple perspective. J Mol Recognit 24(2), 165-181.

Chen, Y., Chan, K.-H., Kang, Y., Chen, H., Luk, H. K. H., Poon, R. W. S., Chan, J. F. W., Yuen, K.-Y., Xia, N., Lau, S. K. P., Woo, P. C. Y., 2015. A sensitive and specific antigen detection assay for Middle East respiratory syndrome coronavirus. Emerg Microbes Infect 4, e26.

Chinnappan, R., Dube, A., Lemay, J.-F., Lafontaine, D. A., 2013. Fluorescence monitoring of riboswitch transcription regulation using a dual molecular beacon assay. Nucleic Acids Research 41(10), e106-e106.

Coleman, C. M., Frieman, M. B., 2015. Growth and quantification of MERS-CoV infection. Current protocols in microbiology 37(1), 15E-12.

Corman, V. M., Landt, O., Kaiser, M., Molenkamp, R., Meijer, A., Chu, D. K. W., Bleicker, T., Brünink, S., Schneider, J., Schmidt, M. L., 2020. Detection of 2019 novel coronavirus (2019-nCoV) by real-time RT-PCR. Eurosurveillance 25(3), 2000045.

Corman, V. M., Muller, M. A., Costabel, U., Timm, J., Binger, T., Meyer, B., Kreher, P., Lattwein, E., Eschbach-Bludau, M., Nitsche, A., Bleicker, T., Landt, O., Schweiger, B., Drexler, J. F., Osterhaus, A. D., Haagmans, B. L., Dittmer, U., Bonin, F., Wolff, T., Drosten, C., 2012. Assays for laboratory confirmation of novel human coronavirus (hCoV-EMC) infections. Euro Surveill 17(49).

Hamre, D., Procknow, J. J., 1966. A new virus isolated from the human respiratory tract. Proc Soc Exp Biol Med 121(1), 190-193.

Kaman, W. E., Hulst, A. G., van Alphen, P. T. W., Roffel, S., van der Schans, M. J., Merkel, T., van Belkum, A., Bikker, F. J., 2011. Peptide-based fluorescence resonance energy transfer protease substrates for the detection and diagnosis of Bacillus species. Analytical chemistry 83(7), 2511-2517.

Kaman, W. E., Voskamp-Visser, I., de Jongh, D. M. C., Endtz, H. P., van Belkum, A., Hays, J. P., Bikker, F. J., 2013. Evaluation of a D-amino-acid-containing fluorescence resonance energy transfer peptide library for profiling prokaryotic proteases. Analytical Biochemistry 441 (1), 38-43.

Kannan, S., Ali, P. S. S., Sheeza, A., Hemalatha, K., 2020. COVID-19 (Novel Coronavirus 2019)-recent trends. Eur. Rev. Med. Pharmacol. Sci 24(4), 2006-2011.

Keightley, M. C., Sillekens, P., Schippers, W., Rinaldo, C., George, K. S., 2005. Real-time NASBA detection of SARS-associated coronavirus and comparison with real-time reverse transcription-PCR. Journal of medical virology 77(4), 602-608.

Kustin, T., Ling, G., Sharabi, S., Ram, D., Friedman, N., Zuckerman, N., Bucris, E. D., Glatman-Freedman, A., Stern, A., Mandelboim, M., 2019. A method to identify respiratory virus infections in clinical samples using next-generation sequencing. Scientific reports 9(1), 2606-2606.

Lam, H., Oh, D.-C., Cava, F., Takacs, C. N., Clardy, J., de Pedro, M. A., Waldor, M. K., 2009. D-Amino Acids Govern Stationary Phase Cell Wall Remodeling in Bacteria. Science 325(5947), 1552.

Lu, X., Whitaker, B., Sakthivel, S. K., Kamili, S, Rose, L. E., Lowe, L., Mohareb, E., Elassal, E. M., Al-sanouri, T., Haddadin, A., Erdman, D. D., 2014. Real-time reverse transcription-PCR assay panel for Middle East respiratory syndrome coronavirus. J Clin Microbiol 52(1), 67-75.

Maeda, H., 1996. Role of microbial proteases in pathogenesis. Microbiol Immunol 40(10), 685-699.

Raja, C., Ferner, J., Dietrich, U., Avilov, S., Ficheux, D., Darlix, J.-L., de Rocquigny, H., Schwalbe, H., Mély, Y., 2006. A Tryptophan-Rich Hexapeptide Inhibits Nucleic Acid Destabilization Chaperoned by the HIV-1 Nucleocapsid Protein. Biochemistry 45(30), 9254-9265.

Rut, W., Groborz, K., Zhang, L., Sun, X., Zmudzinski, M., Hilgenfeld, R., Drag, M., 2020. Substrate specificity profiling of SARS-CoV-2 Mpro protease provides basis for anti-COVID-19 drug design. Biorxiv.

Seo, G., Lee, G., Kim, M. J., Baek, S.-H., Choi, M., Ku, K. B., Lee, C.-S., Jun, S., Park, D., Kim, H. G., Kim, S.-J., Lee, J.-O., Kim, B. T., Park, E. C., Kim, S. I., 2020. Rapid Detection of COVID-19 Causative Virus (SARS-CoV-2) in Human Nasopharyngeal Swab Specimens Using Field-Effect Transistor-Based Biosensor. ACS Nano 14(4), 5135-5142.

Song, Y., Song, J., Wei, X., Huang, M., Sun, M., Zhu, L., Lin, B., Shen, H., Zhu, Z., Yang, C., 2020. Discovery of Aptamers Targeting Receptor-Binding Domain of the SARS-CoV-2 Spike Glycoprotein.

Udugama, B., Kadhiresan, P., Kozlowski, H. N., Malekjahani, A., Osborne, M., Li, V. Y. C., Chen, H., Mubareka, S., Gubbay, J. B., Chan, W. C. W., 2020. Diagnosing COVID-19: the disease and tools for detection. ACS nano 14(4), 3822-3835.

Van de Plassche, M., Barniol-Xicota, M., Verhelst, S., 2020. Peptidyl Acyloxymethyl Ketones as Activity-Based Probes for the Main Protease of SARS-CoV-2. van Kasteren, P. B., van der Veer, B., van den Brink, S., Wijsman, L., de Jonge, J., van den Brandt, A., Molenkamp, R., Reusken, C. B. E. M., Meijer, A., 2020. Comparison of commercial RT-PCR diagnostic kits for COVID-19. Journal of Clinical Virology, 104412.

Zhu, W., Xu, M., Chen, C. Z., Guo, H., Shen, M., Hu, X., Shinn, P., Klumpp-Thomas, C., Michael, S. G., Zheng, W., 2020. Identification of SARS-CoV-2 3CL protease inhibitors by a quantitative high-throughput screening. ACS pharmacology & translational science 3(5), 1008-1016.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for detecting a SARS-Cov-2 protease in a biological sample, comprising:
    contacting the biological sample with a fluorescent probe based sensor, wherein the sensor comprises an L-Histidine-D-aspartic acid peptide substrate, a fluorophore, and a quencher molecule; and
    detecting the SARS-Cov-2 protease when an increase in fluorescence is observed.

2. The method of claim 1, wherein the fluorophore is a xanthene dye.

3. The method of claim 2, wherein the fluorophore is fluorescein isothiocyanate (FITC).

4. The method of claim 1, wherein the fluorophore is at the N-terminus of the FRET sensor.

5. The method of claim 1, wherein the fluorophore is coupled to a linker.

6. The method of claim 1, wherein the quencher molecule is a non-fluorescent quencher molecule.

7. The method of claim 6, wherein the quencher molecule is 4-(4'-dimethylaminophenylazo)-benzoic acid (Dabcyl).

8. The method of claim 1, wherein the quencher molecule is at the C-terminus of the FRET sensor.

9. The method of claim 1, wherein the quencher molecule is coupled to lysine.

10. The method of claim 1, wherein the biological sample is respiratory mucosa.

* * * * *